United States Patent
Kim et al.

(10) Patent No.: US 9,235,886 B2
(45) Date of Patent: Jan. 12, 2016

(54) METHOD FOR TESTING ORGANIC PATTERN

(71) Applicant: Samsung Display Co., Ltd., Yongin, Gyeonggi-Do (KR)

(72) Inventors: Eui-Gyu Kim, Yongin (KR); Dae-Sik Jang, Yongin (KR)

(73) Assignee: Samsung Display Co., Ltd., Samsung-ro, Giheung-Gu, Yongin-si, Gyeonggi-Do (KR)

( * ) Notice: Subject to any disclaimer, the term of this patent is extended or adjusted under 35 U.S.C. 154(b) by 114 days.

(21) Appl. No.: 14/031,487

(22) Filed: Sep. 19, 2013

(65) Prior Publication Data

US 2014/0254914 A1   Sep. 11, 2014

(30) Foreign Application Priority Data

Mar. 11, 2013   (KR) .................. 10-2013-0025714

(51) Int. Cl.
*G06K 9/00* (2006.01)
*G06T 7/00* (2006.01)

(52) U.S. Cl.
CPC ....... *G06T 7/001* (2013.01); *G06T 2207/30121* (2013.01)

(58) Field of Classification Search
None
See application file for complete search history.

(56) References Cited

U.S. PATENT DOCUMENTS

2004/0017162 A1*  1/2004  Sato et al. .................. 315/169.3
2006/0133660 A1*  6/2006  Ogi et al. ..................... 382/149

FOREIGN PATENT DOCUMENTS

| JP | 2009-158328 | 7/2009 |
| KR | 10-2005-0053426 | 6/2005 |
| KR | 10-0768212 | 10/2007 |

* cited by examiner

*Primary Examiner* — Eueng-Nan Yeh
(74) *Attorney, Agent, or Firm* — Robert E. Bushnell, Esq.

(57) ABSTRACT

A method for testing an organic pattern including: forming an organic pattern on a test substrate through a mask; acquiring a test image by photographing a predetermined test area of the test substrate; and checking whether an edge of the organic pattern displayed to the test image goes over an edge of a virtual test figure.

16 Claims, 8 Drawing Sheets

METHOD FOR TESTING ORGANIC PATTERN

CLAIM PRIORITY

This application makes reference to, incorporates the same herein, and claims all benefits accruing under 35 U.S.C. §119 from an application earlier filed in the Korean Intellectual Property Office on 11 Mar. 2013 and there duly assigned Serial No. 10-2013-0025714.

BACKGROUND OF THE INVENTION

1. Field of the Invention

The described technology relates generally to a method for testing an organic pattern.

2. Description of the Related Art

A display device is a device for displaying an image, and an organic light emitting diode (OLED) display recently has received attention.

The organic light emitting diode display has a self light emitting characteristic, and it has reduced thickness and weight since it requires no additional light source, differing from a liquid crystal display device. Also, the organic light emitting diode display shows high quality characteristics such as power consumption, high luminance, and a high reaction speed.

The above information disclosed in this Related Art section is only for enhancement of understanding of the background of the described technology and therefore it may contain information that does not form the prior art that is already known in this country to a person of ordinary skill in the art.

SUMMARY OF THE INVENTION

The described technology has been made in an effort to provide a method for easily testing an organic pattern deposited on a substrate through a mask.

An exemplary embodiment provides a method for testing an organic pattern including: forming an organic pattern on a test substrate through a mask; acquiring a test image by photographing a predetermined test area of the test substrate; and checking whether an edge of the organic pattern displayed to the test image goes over an edge of a virtual test figure.

The test substrate includes a pattern area in which a first pixel pattern, a second pixel pattern, and a third pixel pattern neighbor each other, and a non-pattern area neighboring the pattern area, and the acquiring of a test image may be performed by photographing the test area including the pattern area and the non-pattern area.

The forming of an organic pattern on a test substrate through a mask includes: forming a plurality of first organic patterns for covering the first pixel pattern of the pattern area and a first section of the non-pattern area on the test substrate through a first mask; forming a plurality of second organic patterns for covering the second pixel pattern of the pattern area and a second section of the non-pattern area on the test substrate through a second mask; and forming a plurality of third organic patterns for covering the third pixel pattern of the pattern area and a third section of the non-pattern area on the test substrate through a third mask.

The checking of whether an edge of the organic pattern displayed to the test image goes over an edge of a virtual test figure includes: checking whether an edge of the first organic pattern goes over an edge of a virtual first test figure displayed to the first section of the non-pattern area; checking whether an edge of the second organic pattern goes over an edge of a virtual second test figure displayed to the second section of the non-pattern area; and checking whether an edge of the third organic pattern goes over an edge of a virtual third test figure displayed to the third section of the non-pattern area.

Depths of the first test figure, the second test figure, and the third test figure in a first direction correspond to depths of the first pixel pattern, the second pixel pattern, and the third pixel pattern in the first direction.

The first test figure may be separated from the first pixel pattern with the second organic pattern therebetween, the second test figure may be separated from the second pixel pattern with the first organic pattern therebetween, and the third test figure may be separated from the third pixel pattern with the second organic pattern therebetween.

The first test figure, the second test figure, and the third test figure respectively have a figure shape of a different size.

The first test figure may be provided between the neighboring first pixel patterns, the second test figure may be provided between the neighboring second pixel patterns, and the third test figure may be provided between the neighboring third pixel patterns.

The first test figure, the second test figure, and the third test figure respectively have a figure shape of a same size.

The second organic patterns are extended in a first direction and are separated from each other in a second direction crossing the first direction, the first organic patterns are separated from the third organic patterns in the second direction with the second organic patterns therebetween, and the third organic patterns neighbor the first organic pattern in the first direction. The checking of whether an edge of the organic pattern displayed to the test image goes over an edge of a virtual test figure includes: checking whether each edge of the first pixel pattern may be provided inside two virtual first pixel figures disposed in the second direction, and checking whether a first edge and a second edge of a virtual fourth test figure having a center area separated from the first pixel figure in the first direction and extended in the second direction go over an edge of the second organic pattern covering the second pixel pattern and an edge of the second organic pattern covering the second section; checking whether each edge of the second pixel pattern may be provided inside two virtual second pixel figures disposed in the second direction, and checking whether a first edge and a second edge of a virtual fifth test figure having a center area separated from the second pixel figure in the first direction and extended in the second direction go over an edge of the third organic pattern covering the third pixel pattern and an edge of the first organic pattern covering the first section; and checking whether each edge of the third pixel pattern may be provided inside two virtual third pixel figures disposed in the second direction, and checking whether a first edge and a second edge of a virtual sixth test figure having a center area separated from the third pixel figure in the first direction and extended in the second direction go over an edge of the second organic pattern covering the second pixel pattern and an edge of the second organic pattern covering the second section.

The first organic patterns are separated from each other in the first direction with the third organic patterns therebetween, and the checking of whether an edge of the organic pattern displayed to the test image goes over an edge of a virtual test figure further includes: checking whether each edge of the first pixel pattern may be provided inside two virtual fourth pixel figures disposed in the first direction, and checking whether a first edge and a second edge of a virtual seventh test figure having a center area separated from the fourth pixel figure in the second direction and extended in the first direction go over edges of the two first organic patterns that are separated with the third organic pattern therebetween; and checking whether each edge of the third pixel pattern may be provided inside two virtual fifth pixel figures disposed in the first direction, and checking whether a first edge and a second edge of a virtual eighth test figure having a center area separated from the fifth pixel figure in the second direction and extended in the first direction go over edges of the two third organic patterns separated with the first organic pattern therebetween.

According to the embodiment, the method for easily testing an organic pattern deposited on a substrate through a mask is provided.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, in which like reference symbols indicate the same or similar components, wherein.

DETAILED DESCRIPTION OF THE INVENTION

Figure 1:
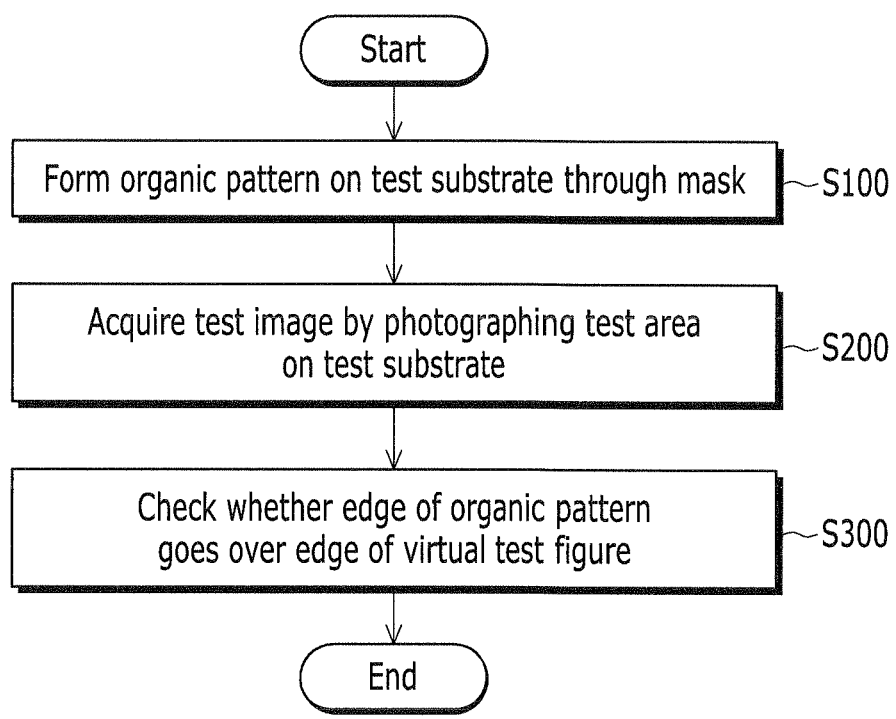
FIG. 1 shows a flowchart of a method for testing an organic pattern according to a first exemplary embodiment.

The example embodiments are described more fully hereinafter with reference to the accompanying drawings. The inventive concept may, however, be embodied in many different forms and should not be construed as limited to the example embodiments set forth herein. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like or similar reference numerals refer to like or similar elements throughout. As used herein, the term "and/or" includes any and all combinations of one or more of the associated listed items.

It will be understood that, although the terms first, second, third etc. may be used herein to describe various elements, components, regions, layers, patterns and/or sections, these elements, components, regions, layers, patterns and/or sections should not be limited by these terms. These terms are only used to distinguish one element, component, region, layer pattern or section from another region, layer, pattern or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross sectional illustrations that are schematic illustrations of illustratively idealized example embodiments (and intermediate structures) of the inventive concept. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. The regions illustrated in the figures are schematic in nature and their shapes are not intended to illustrate the actual shape of a region of a device and are not intended to limit the scope of the inventive concept.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In general, the organic light emitting diode display includes a substrate and an organic pattern patterned as an organic layer for each pixel. When the organic light emitting diode display is manufactured, a method for testing the organic pattern is performed.

A conventional method for testing an organic pattern determines whether there is a problem therewith through visual testing of the organic pattern deposited on the substrate through a mask by using a high-resolution microscope, and corrects an evaporation source by evaporating the substrate, the mask, or the organic material to the mask side when a problem occurs on the organic pattern.

Referring to FIG. 1 to FIG. 5, a method for testing an organic pattern according to a first exemplary embodiment will now be described.

Figure 4:
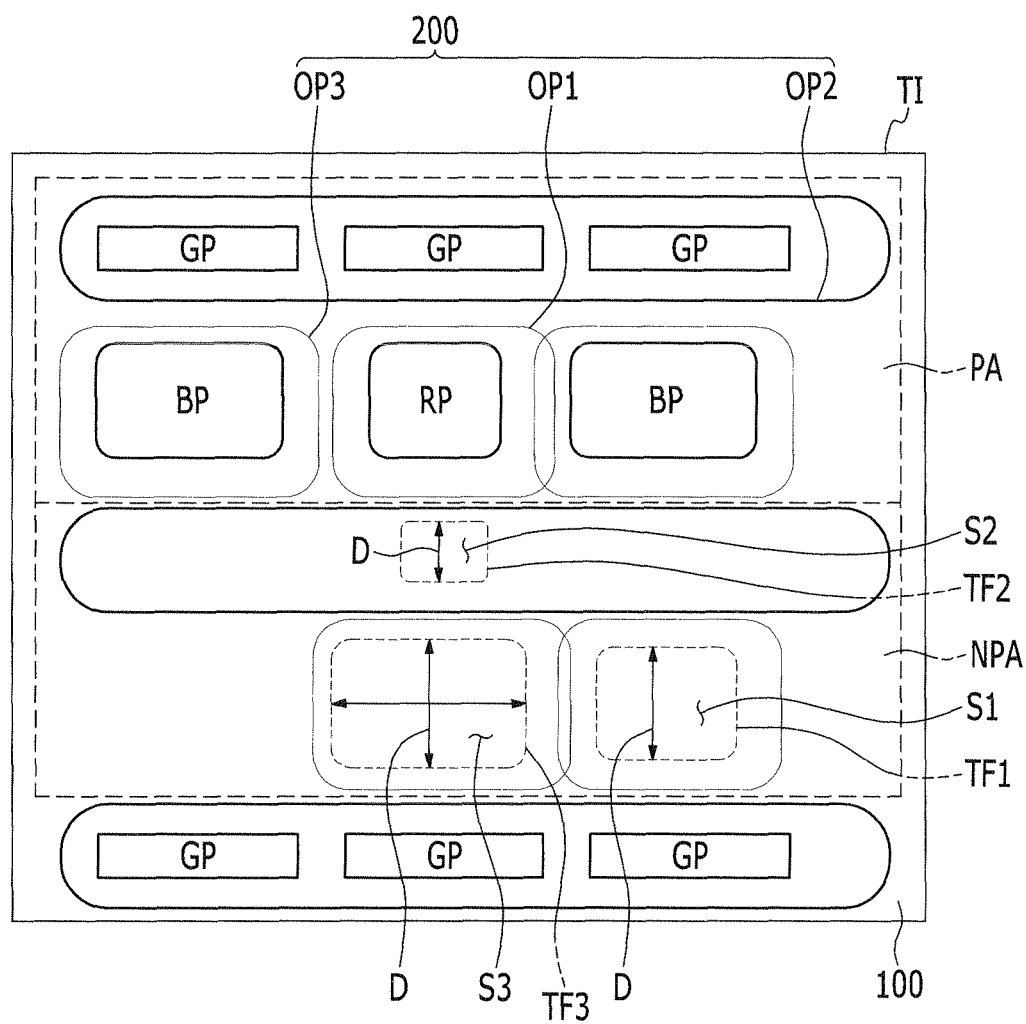
Figure 5:
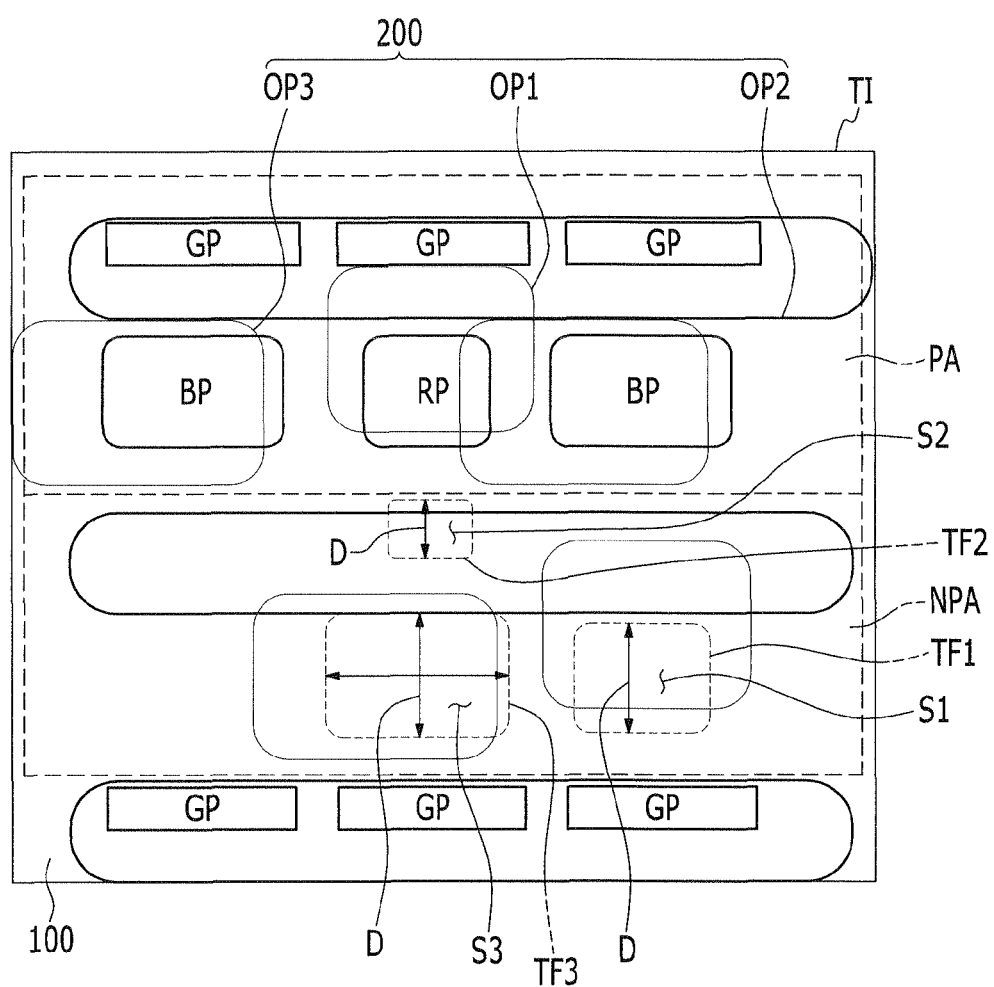

FIG. 1 shows a flowchart of a method for testing an organic pattern according to a first exemplary embodiment. FIG. 2 to FIG. 5 show a method for testing an organic pattern according to a first exemplary embodiment. FIG. 4 and FIG. 5 show a test image acquired by photographing a test area of a test substrate on which an organic pattern is formed.

As shown in FIG. 1, an organic pattern 200 may be formed on a test substrate 100 through a mask 300 (S100).

In detail, the test substrate 100 is not a substrate to be manufactured as an organic light emitting diode (OLED) display, but it is a substrate for testing. That is, the test substrate 100 is an additional substrate for testing formation of the organic pattern 200 through the mask 300. As shown in FIG. 4, the test substrate 100 includes: a pattern area (PA) in which a first pixel pattern (RP), a second pixel pattern (GP), and a third pixel pattern (BP) that neighbor each other and correspond to a first pixel, a second pixel, and a third pixel of a substrate to be manufactured as an organic light emitting diode display; and a non-pattern area (NPA) that neighbors the pattern area (PA). The non-pattern area (NPA) of the test substrate 100 includes a first section (S1), a second section (S2), and a third section (S3) corresponding to the first pixel pattern (RP), the second pixel pattern (GP), and the third pixel pattern (BP), respectively.

Figure 2:
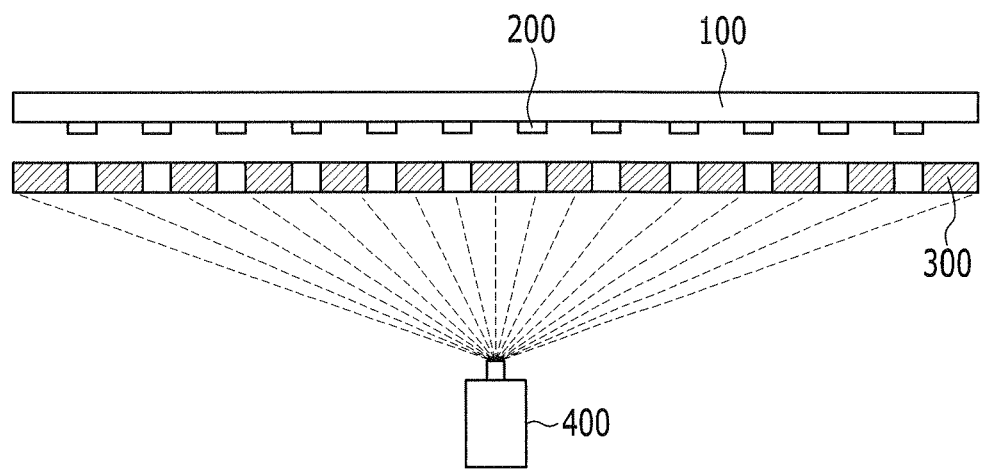
FIG. 2 to FIG. 5 shows a method for testing an organic pattern according to a first exemplary embodiment.

As shown in FIG. 2, the organic pattern 200 may be formed on the test substrate 100 through the mask 300 by depositing an organic material on the test substrate 100 through the mask 300 from a deposition source 400.

As shown in FIG. 4, the organic pattern 200 includes a first organic pattern (OP1), a second organic pattern (OP2), and a third organic pattern (OP3) that neighbor each other which are formed on the test substrate 100 through a first mask, a second mask, and a third mask that are different from each other.

In detail, the formation of the organic pattern 200 on the test substrate 100 through the mask 300 includes: forming a plurality of first organic patterns (OP1) for covering the first pixel pattern (RP) of the pattern area (PA) of the test substrate 100 and the first section (S1) of the non-pattern area (NPA) that corresponds to the first pixel pattern (RP) on the test substrate 100 through the first mask; forming a plurality of second organic patterns (OP2) for covering the second pixel pattern (GP) of the pattern area (PA) of the test substrate 100 and the second section (S2) of the non-pattern area (NPA) that corresponds to the second pixel pattern (GP) on the test substrate 100 through the second mask; and forming a plurality of third organic patterns (OP3) for covering the third pixel pattern (BP) of the pattern area (PA) of the test substrate 100 and the third section (S3) of the non-pattern area (NPA) that corresponds to the third pixel pattern (BP) on the test substrate 100 through the third mask.

For example, the first organic pattern (OP1) functions as an organic emission layer for emitting red light on the substrate to be manufactured as the organic light emitting diode display, the second organic pattern (OP2) functions as an organic emission layer for emitting green light on the substrate to be manufactured as the organic light emitting diode display, and the third organic pattern (OP3) functions as an organic emission layer for emitting blue light on the substrate to be manufactured as the organic light emitting diode display.

Figure 3:
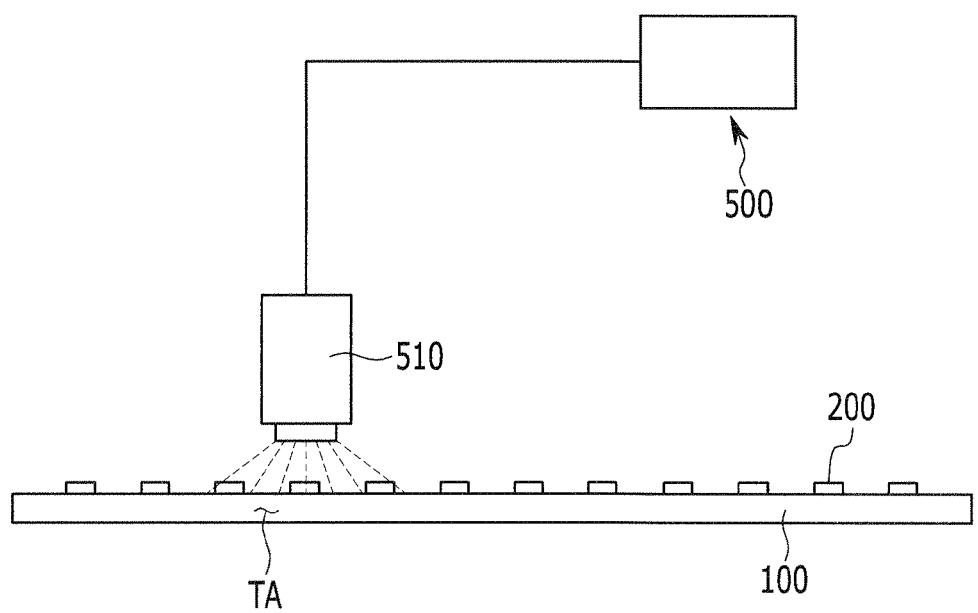

As shown in FIG. 3, a test image may be acquired by photographing a predetermined test area (TA) of the test substrate 100 (S200).

In detail, the predetermined test area (TA) of the test substrate 100 may be photographed by using a photographing device 500 including a camera 510 such as a CCD camera to acquire a test image (TI) shown in FIG. 4 or FIG. 5.

As shown in FIG. 4, acquisition of the test image (TI) may be performed by photographing the test area (TA) of the test substrate 100 including the pattern area (PA) and the non-pattern area (NPA) of the test substrate 100.

As shown in FIG. 4 and FIG. 5, an edge of the organic pattern 200 goes over an edge of a virtual test figure (S300).

FIG. 4 shows a test image (TI) with no generation of deposition errors at the first organic pattern (OP1), the second organic pattern (OP2), and the third organic pattern (OP3) that are deposited on the test substrate 100 through the mask 300, and FIG. 5 shows a test image (TI) of generation of deposition errors at the first organic pattern (OP1), the second organic pattern (OP2), and the third organic pattern (OP3) that are deposited on the test substrate 100 through the mask 300.

In detail, a virtual first test figure (TF1), a second test figure (TF2), and a third test figure (TF3) are displayed in the test image (TI) corresponding to the first section (S1), the second section (S2), and the third section (S3) of the non-pattern area (NPA), and respective depths (D) in one direction of the first test figure (TF1), the second test figure (TF2), and the third test figure (TF3) are the same as depths (D) in one direction of the first pixel pattern (RP), the second pixel pattern (GP), and the third pixel pattern (BP).

The first test figure (TF1) may be separated from the first pixel pattern (RP) with the second organic pattern (OP2) therebetween The second test figure (TF2) may be separated from the second pixel pattern (GP) with the first organic pattern (OP1) therebetween. The third test figure (TF3) may be separated from the third pixel pattern (BP) with the second organic pattern (OP2) therebetween. The first test figure (TF1), the second test figure (TF2), and the third test figure (TF3) have figure shapes with different sizes corresponding to the first pixel pattern (RP), the second pixel pattern (GP), and the third pixel pattern (BP) since the first pixel pattern (RP), the second pixel pattern (GP), and the third pixel pattern (BP) have different figures.

The first test figure (TF1), the second test figure (TF2), and the third test figure (TF3) respectively have a substantially quadrangular shape, and without being restricted to this, they can have various figure shapes such as a triangle, a pentagon, or a circle.

It may be checked whether an edge of the first organic pattern (OP1) goes over an edge of the virtual first test figure (TF1) displayed to the first section (S1) of the non-pattern area (NPA). As shown in FIG. 4, when the edge of the first organic pattern (OP1) does not go over the edge of the virtual first test figure (TF1) displayed to the first section (S1) of the non-pattern area (NPA), it is confirmed that no deposition error may be generated on the first organic pattern (OP1), and this may be then reported to a user. On the contrary, as shown in FIG. 5, when the edge of the first organic pattern (OP1) goes over the edge of the virtual first test figure (TF1) displayed to the first section (S1) of the non-pattern area (NPA), it is confirmed that the deposition error may be generated on the first organic pattern (OP1), and this may be then reported to the user.

It is checked whether an edge of the second organic pattern (OP2) goes over an edge of the virtual second test figure (TF2) displayed to the second section (S2) of the non-pattern area (NPA). As shown in FIG. 4, when the edge of the second organic pattern (OP2) does not go over the edge of the virtual second test figure (TF2) displayed to the second section (S2) of the non-pattern area (NPA), it is confirmed that no deposition error may be generated to the second organic pattern (OP2), and this is then reported to the user. On the contrary, as shown in FIG. 5, when the edge of the second organic pattern (OP2) goes over the edge of the virtual second test figure (TF2) displayed to the second section (S2) of the non-pattern area (NPA), it is confirmed that the deposition error is generated to the second organic pattern (OP2), and this may be then reported to the user.

It is checked whether an edge of the third organic pattern (OP3) goes over an edge of the virtual third test figure (TF3)

displayed to the third section (S3) of the non-pattern area (NPA). As shown in FIG. 4, when the edge of the third organic pattern (OP3) does not go over the edge of the virtual third test figure (TF3) displayed to the third section (S3) of the non-pattern area (NPA), it is confirmed that no deposition error may be generated to the third organic pattern (OP3), and this may be then reported to the user. On the contrary, as shown in FIG. 5, when the edge of the third organic pattern (OP3) goes over the edge of the virtual third test figure (TF3) displayed to the third section (S3) of the non-pattern area (NPA), it is confirmed that the deposition error is generated to the third organic pattern (OP3), and this may be then reported to the user.

The above-described checking whether the edge of the organic pattern 200 goes over the edge of the virtual test figure may be performed by a controller including a terminal, and the checking of generation of the deposition error performed by the controller may be displayed to the user through a display connected to the controller.

Accordingly, the method for testing an organic pattern according to the first exemplary embodiment photographs the test area (TA) including the pattern area (PA) and the non-pattern area (NPA) of the test substrate 100, a designated position, to acquire the test image (TI) that corresponds to the test area (TA), and the method uses the virtual first test figure (TF1), the second test figure (TF2), and the third test figure (TF3) displayed to the non-pattern area (NPA) corresponding to the first pixel pattern (RP), the second pixel pattern (GP), and the third pixel pattern (BP) included in the pattern area (PA) of the test image (TI) to check whether the deposition error may be generated to the first organic pattern (OP1), the second organic pattern (OP2), and the third organic pattern (OP3), thereby easily testing the organic pattern 200 deposited to the test substrate 100.

That is, the method for testing an organic pattern for easily testing the deposition errors of the first organic pattern (OP1), the second organic pattern (OP2), and the third organic pattern (OP3) formed on the single test substrate 100 rather than testing the deposition error on the single organic pattern 200 may be provided.

This is information for changing process environments (e.g., a position of the substrate, a shape of the mask, a disposal of the mask, or a disposal of the deposition source) for forming one of the first organic pattern (OP1), the second organic pattern (OP2), and the third organic pattern (OP3) to which the deposition error may be generated when the first organic pattern (OP1), the second organic pattern (OP2), and the third organic pattern (OP3) are respectively deposited on the substrate to be manufactured as the organic light emitting diode display, and it may be provided to a manufacturer for manufacturing the organic light emitting diode display.

Figure 6:
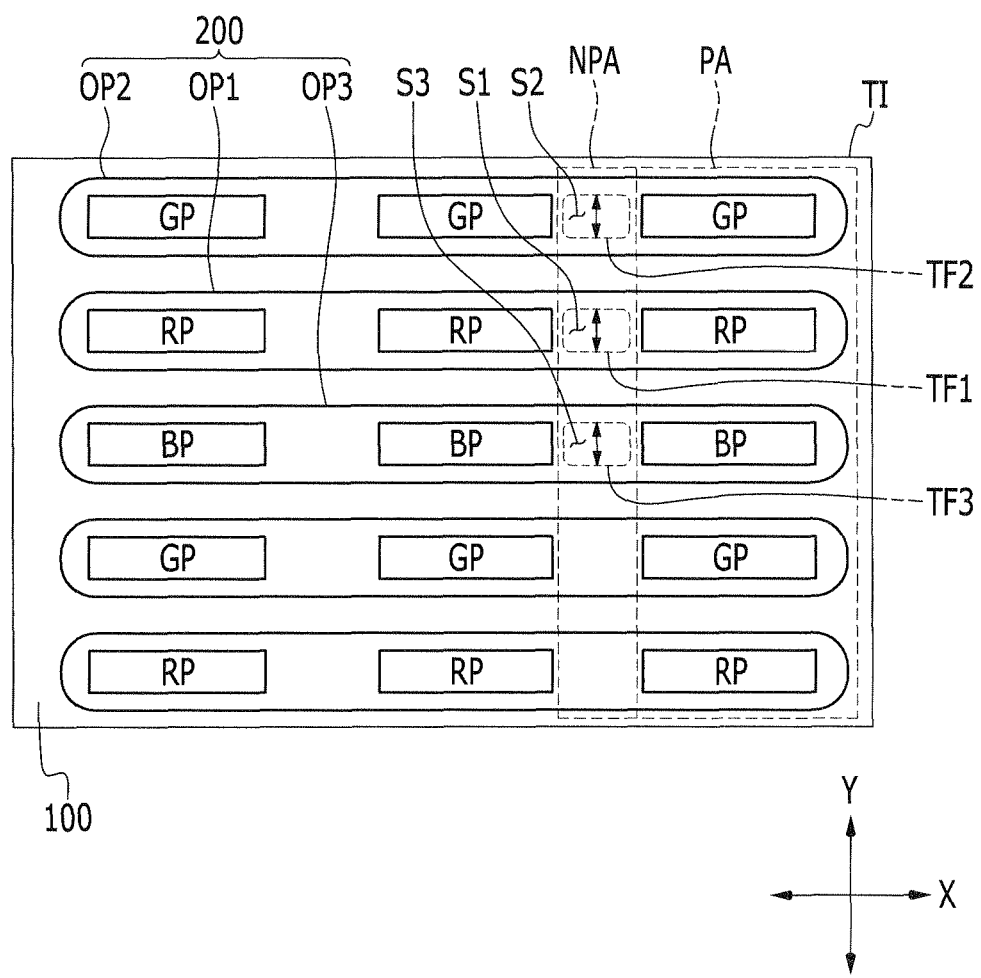
FIG. 6 shows a method for testing an organic pattern according to a second exemplary embodiment.

Referring to FIG. 6, a method for testing an organic pattern according to a second exemplary embodiment will now be described.

Hereafter, only characteristic parts that are different from the first exemplary embodiment will be described, and parts whose descriptions are omitted are described in accordance with the first exemplary embodiment. The second exemplary embodiment has the same reference numerals for the same constituent elements as the first exemplary embodiment for better comprehension and ease of description.

FIG. 6 shows a method for testing an organic pattern according to a second exemplary embodiment. FIG. 6 shows a test image acquired by photographing a test area of a test substrate on which an organic pattern is formed.

An organic pattern may be formed on the test substrate 100 through a mask.

A predetermined test area (TA) of the test substrate 100 may be photographed to acquire a test image.

As shown in FIG. 6, it is checked whether an edge of the organic pattern 200 goes over an edge of a virtual test figure.

In detail, the second organic pattern (OP2), the first organic pattern (OP1), and the third organic pattern (OP3) formed on the test substrate 100 are extended in a first direction X, and they are sequentially separately disposed in a second direction Y crossing the first direction X.

A virtual first test figure (TF1), a second test figure (TF2), and a third test figure (TF3) are displayed in the test image (TI) corresponding to the first section (S1), the second section (S2), and the third section (S3) of the non-pattern area (NPA). The first test figure (TF1) may be provided between the neighboring first pixel patterns (RP), the second test figure (TF2) may be provided between the neighboring second pixel patterns (GP), and the third test figure (TF3) may be provided between the neighboring third pixel patterns (BP). The first test figure (TF1), the second test figure (TF2), and the third test figure (TF3) respectively have a figure shape of the same size.

It is checked whether an edge of the first organic pattern (OP1) goes over an edge of the virtual first test figure (TF1) displayed to the first section (S1) of the non-pattern area (NPA). As shown in FIG. 6, when the edge of the first organic pattern (OP1) does not go over the edge of the virtual first test figure (TF1) displayed to the first section (S1) of the non-pattern area (NPA), it is confirmed that no deposition error is generated on the first organic pattern (OP1), and this may be then reported to the user. On the contrary, when the edge of the first organic pattern (OP1) goes over the edge of the virtual first test figure (TF1) displayed to the first section (S1) of the non-pattern area (NPA), it is confirmed that the deposition error is generated on the first organic pattern (OP1), and this may be then reported to the user.

It is checked whether an edge of the second organic pattern (OP2) goes over an edge of the virtual second test figure (TF2) displayed to the second section (S2) of the non-pattern area (NPA). As shown in FIG. 6, when the edge of the second organic pattern (OP2) does not go over the edge of the virtual second test figure (TF2) displayed to the second section (S2) of the non-pattern area (NPA), it is confirmed that no deposition error is generated to the second organic pattern (OP2), and this may be then reported to the user. On the contrary, when the edge of the second organic pattern (OP2) goes over the edge of the virtual second test figure (TF2) displayed to the second section (S2) of the non-pattern area (NPA), it is confirmed that the deposition error is generated to the second organic pattern (OP2), and this may be then reported to the user.

It may be checked whether an edge of the third organic pattern (OP3) goes over an edge of the virtual third test figure (TF3) displayed to the third section (S3) of the non-pattern area (NPA). As shown in FIG. 6, when the edge of the third organic pattern (OP3) does not go over the edge of the virtual third test figure (TF3) displayed to the third section (S3) of the non-pattern area (NPA), it is confirmed that no deposition error is generated to the third organic pattern (OP3), and this may be then reported to the user. On the contrary, when the edge of the third organic pattern (OP3) goes over the edge of the virtual third test figure (TF3) displayed to the third section (S3) of the non-pattern area (NPA), it is confirmed that the deposition error is generated to the third organic pattern (OP3), and this may be thenreported to the user.

The above-described checking whether the edge of the organic pattern 200 goes over the edge of the virtual test figure is performed by a controller including a terminal, and the checking of generation of the deposition error performed by the controller is displayed to the user through a display connected to the controller.

Accordingly, the method for testing an organic pattern according to the second exemplary embodiment photographs the test area (TA) including the pattern area (PA) and the non-pattern area (NPA) of the test substrate 100, a designated position, to acquire the test image (TI) that corresponds to the test area (TA), and it uses the virtual first test figure (TF1), the second test figure (TF2), and the third test figure (TF3) displayed to the non-pattern area (NPA) corresponding to the first pixel pattern (RP), the second pixel pattern (GP), and the third pixel pattern (BP) included in the pattern area (PA) of the test image (TI) to check whether the deposition error is generated to the first organic pattern (OP1), the second organic pattern (OP2), and the third organic pattern (OP3), thereby easily testing the organic pattern 200 deposited to the test substrate 100.

That is, the method for testing an organic pattern for easily testing the deposition error for the first organic pattern (OP1), the second organic pattern (OP2), and the third organic pattern (OP3) formed on the single test substrate 100 rather than testing the deposition error for the single organic pattern 200 is provided.

This is information for changing process environments (e.g., a position of the substrate, a shape of the mask, a disposal of the mask, or a disposal of the deposition source) for forming one of the first organic pattern (OP1), the second organic pattern (OP2), and the third organic pattern (OP3) to which the deposition error is generated when the first organic pattern (OP1), the second organic pattern (OP2), and the third organic pattern (OP3) are respectively deposited on the substrate to be manufactured as the organic light emitting diode display, and it is provided to a manufacturer for manufacturing the organic light emitting diode display.

Figure 7:
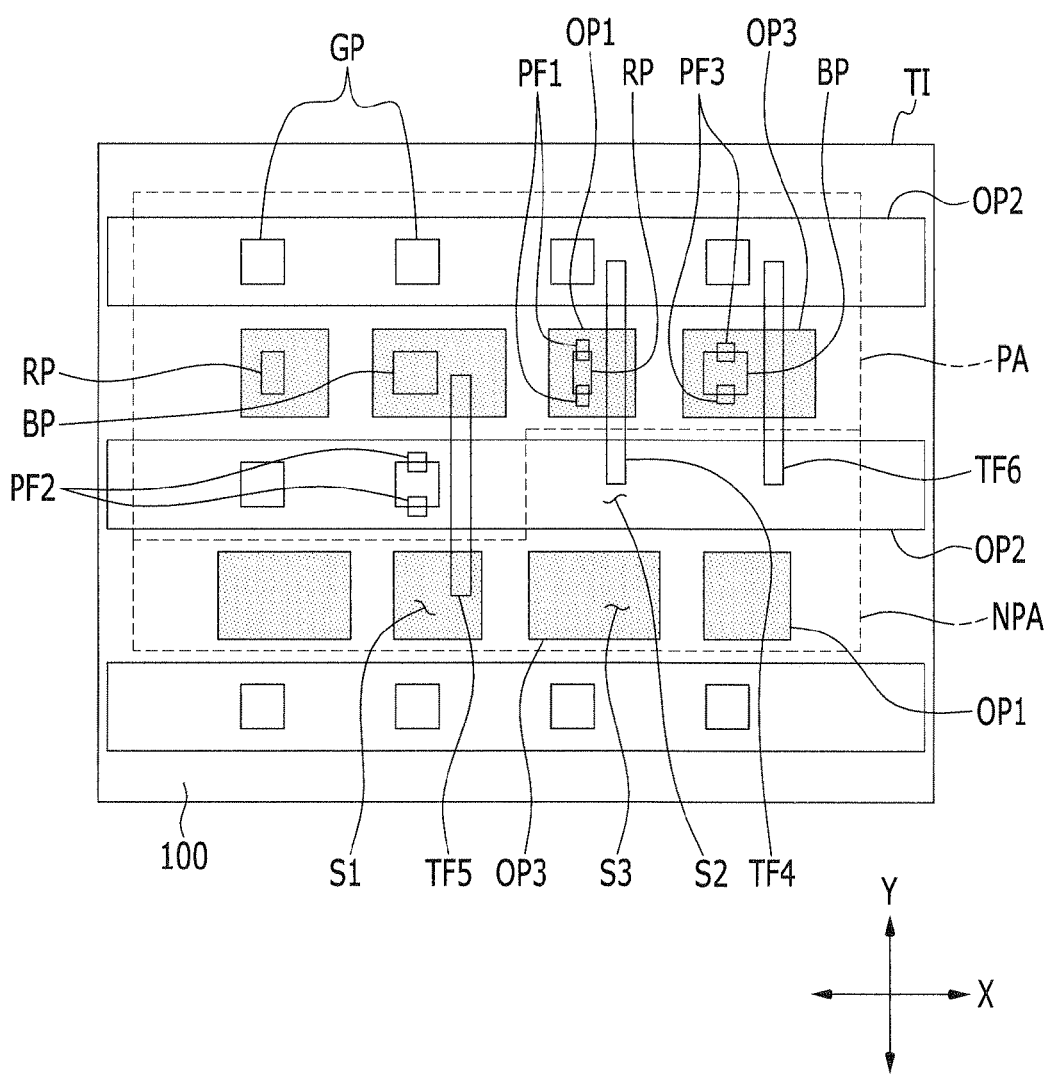
FIG. 7 and FIG. 8 show a method for testing an organic pattern according to a third exemplary embodiment.
Figure 8:
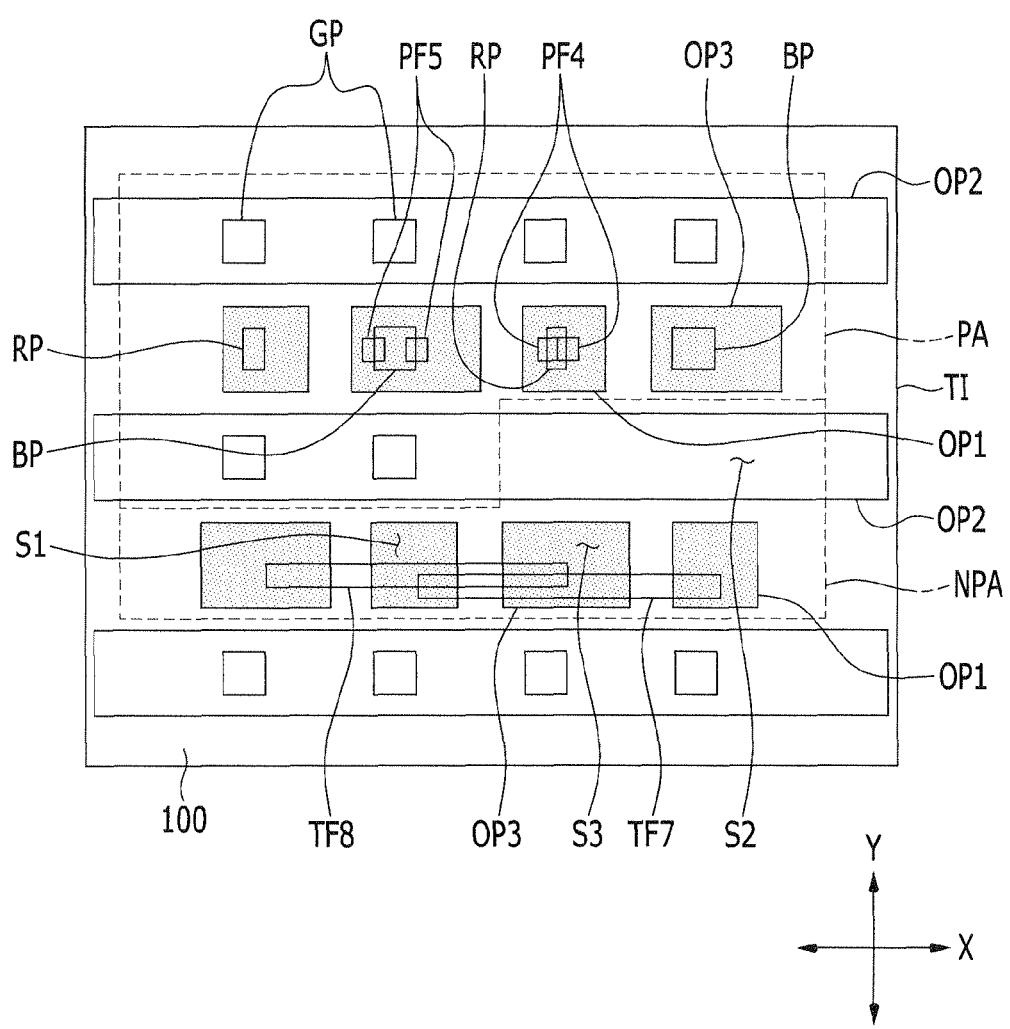

Referring to FIG. 7 and FIG. 8, a method for testing an organic pattern according to a third exemplary embodiment will now be described.

Hereafter, only characteristic parts that are different from the first exemplary embodiment will be described, and parts whose descriptions are omitted are described in accordance with the first exemplary embodiment. The third exemplary embodiment has the same reference numerals for the same constituent elements as the first exemplary embodiment for better comprehension and ease of description.

FIG. 7 and FIG. 8 show a method for testing an organic pattern according to a third exemplary embodiment. FIG. 7 and FIG. 8 show test images acquired by photographing a test area of a test substrate on which an organic pattern is formed.

An organic pattern is formed on the test substrate 100 through a mask.

A predetermined test area (TA) of the test substrate 100 is photographed to acquire a test image.

As shown in FIG. 7 and FIG. 8, it is checked whether an edge of the organic pattern 200 goes over an edge of a virtual test figure.

In detail, the plurality of second organic patterns (OP2) formed on the test substrate 100 are extended in the first direction X and are separated in the second direction Y crossing the first direction X. The first organic patterns (OP1) are mutually separated in the first direction X with the third organic patterns (OP3) therebetween, and the first organic patterns (OP1) are separated from the third organic pattern (OP3) in the second direction Y with the second organic patterns (OP2) therebetween. The third organic patterns (OP3) neighbor the first organic patterns (OP1) in the first direction X.

As shown in FIG. 7, the deposition errors of the first organic pattern (OP1), the second organic pattern (OP2), and the third organic pattern (OP3) are checked in the second direction Y.

It is checked whether each edge of the first pixel pattern (RP) is provided inside two virtual first pixel figures (PF1) disposed in the second direction Y, and it is checked whether a first edge and a second edge of a virtual fourth test figure (TF4) having a center area that is separated from the first pixel figure (PF1) in the first direction X and is extended in the second direction Y go over an edge of the second organic pattern (OP2) covering the second pixel pattern (GP) and an edge of the second organic pattern (OP2) covering the second section (S2). When the first edge and the second edge of the fourth test figure (TF4) do not go over the edges of the second organic patterns (OP2) that neighbor each other for covering the second pixel pattern (GP) and the second section (S2) with reference to the first pixel figure (PF1) for the first pixel pattern (RP), it is confirmed that no deposition error is generated in the second direction Y to the second organic patterns (OP2) that neighbor each other with reference to the first pixel pattern (RP), and this may be then reported to the user. On the contrary, when the first edge and the second edge of the fourth test figure (TF4) go over the edges of the second organic patterns (OP2) that neighbor each other for covering the second pixel pattern (GP) and the second section (S2) with reference to the first pixel figure (PF1) for the first pixel pattern (RP), it is confirmed that the deposition error is generated in the second direction Y to the second organic patterns (OP2) that neighbor each other with reference to the first pixel pattern (RP), and this may be the nreported to the user.

That is, the deposition errors of the mutually-neighboring second pixel patterns (GP) in the second direction Y are checked with reference to the first pixel pattern (RP) by using the first pixel figure (PF1) and the fourth test figure (TF4).

It is checked whether each edge of the second pixel pattern (GP) is provided inside two virtual second pixel figures (PF2) disposed in the second direction Y, and it is checked whether a first edge and a second edge of a virtual fifth test figure (TF5) having a center area that is separated from the second pixel figure (PF2) in the first direction X and is extended in the second direction Y go over an edge of the third organic pattern (OP3) covering the third pixel pattern (BP) and an edge of the first organic pattern (OP1) covering the first section (S1). When a first edge and a second edge of the fifth test figure (TF5) do not go over an edge of the third organic pattern (OP3) covering the third pixel pattern (BP) and an edge of the first organic pattern (OP1) covering the first section (S1) with reference to the second pixel figure (PF2) for the second pixel pattern (GP), it is confirmed that no deposition error is generated to the mutually-separated third organic pattern (OP3) and first organic pattern (OP1) in the second direction Y with reference to the second pixel pattern (GP), and this may be then reported to the user. On the contrary, when the first edge and the second edge of the fifth test figure (TF5) go over the edge of the third organic pattern (OP3) covering the third pixel pattern (BP) and the edge of the first organic pattern (OP1) covering the first section (S1) with reference to the second pixel figure (PF2) for the second pixel pattern (GP), it is confirmed that the deposition error is generated in the second direction Y to the third organic pattern (OP3) and first organic pattern (OP1) that are separated from each other with reference to the second pixel pattern (GP), and this may be then reported to the user.

That is, the deposition errors of the mutually-separated third organic pattern (OP3) and first organic pattern (OP1) in the second direction Y are checked with reference to the second pixel pattern (GP) by using the second pixel figure (PF2) and the fifth test figure (TF5).

It is checked whether each edge of the third pixel pattern (BP) is provided inside two virtual third pixel figures (PF3) disposed in the second direction Y, and it is checked whether a first edge and a second edge of a virtual sixth test figure (TF6) having a center area that is separated from the third pixel figure (PF3) in the first direction X and is extended in the second direction Y go over the edge of the second organic pattern (OP2) covering the second pixel pattern (GP) and the edge of the second organic pattern (OP2) covering the second section (S2). When the first edge and the second edge of the sixth test figure (TF6) do not go over each edge of the mutually neighboring second organic patterns (OP2) covering the second pixel pattern (GP) and the second section (S2) with reference to the third pixel figure (PF3) for the third pixel pattern (BP), it is confirmed that no deposition error is generated in the second direction Y to the second organic patterns (OP2) that neighbor each other with reference to the third pixel pattern (BP), and this may be then reported to the user. On the contrary, when the first edge and the second edge of the sixth test figure (TF6) go over each edge of the mutually neighboring second organic patterns (OP2) covering the second pixel pattern (GP) and the second section (S2), it is confirmed that the deposition error is generated in the second direction to the second organic patterns (OP2) Y that neighbor each other with reference to the third pixel pattern (BP), and this may be then reported to the user.

That is, the deposition errors of the mutually neighboring second pixel patterns (GP) in the second direction Y are checked with reference to the third pixel pattern (BP) by using the third pixel figure (PF3) and the sixth test figure (TF6).

As shown in FIG. 8, the deposition errors of the first organic pattern (OP1) and the third organic pattern (OP3) in the first direction X are checked It is checked whether each edge of the first pixel pattern (RP) is provided inside two virtual fourth pixel figures (PF4) disposed in the first direction X, and it is checked whether a first edge and a second edge of a virtual seventh test figure (TF7) having a center area that is separated from the fourth pixel figure (PF4) in the second direction Y and is extended in the first direction X go over each edge of the two first organic patterns (OP1) that are separated from each other with the third organic pattern (OP3) therebetween. When the first edge and the second edge of the seventh test figure (TF7) do not go over each edge of the two first organic patterns (OP1) that are separated from each other with the third organic pattern (OP3) therebetween with reference to the fourth pixel figure (PF4) for the first pixel pattern (RP), it is confirmed that no deposition error is generated in the first direction X to the first organic patterns (OP1) that are separated in the second direction Y with reference to the first pixel pattern (RP) and are separated from each other in the first direction X, and this may be then reported to the user. On the contrary, when the first edge and the second edge of the seventh test figure (TF7) go over each edge of the two first organic patterns (OP1) that are separated from each other with the third organic pattern (OP3) therebetween with reference to the fourth pixel figure (PF4) for the first pixel pattern (RP), it is confirmed that the deposition error is generated in the first direction X to the first organic patterns (OP1) that are separated in the second direction Y with reference to the first pixel pattern (RP) and are separated from each other in the first direction X, and this may be then reported to the user.

That is, the deposition errors of the first organic patterns (OP1) in the first direction X that are separated in the second direction Y with reference to the first pixel pattern (RP) and are separated from each other in the first direction X are checked by using the fourth pixel figure (PF4) and the seventh test figure (TF7).

It is checked whether each edge of the third pixel pattern (BP) is provided inside two virtual fifth pixel figures (PF5) disposed in the first direction X, and it is checked whether a first edge and a second edge of a virtual eighth test figure (TF8) having a center area that is separated from the fifth pixel figure (PF5) in the second direction Y and is extended in the first direction X go over edges of two third organic patterns (OP3) that are separated with the first organic pattern (OP1) therebetween. When the first edge and the second edge of the virtual eighth test figure (TF8) do not go over the edges of two third organic patterns (OP3) that are separated with the first organic pattern (OP1) therebetween with reference to the fifth pixel figure (PF5) for the third pixel pattern (BP), it is confirmed that no deposition error is generated in the first direction X to the third organic patterns (OP3) that are separated in the second direction Y with reference to the third pixel pattern (BP) and are separated from each other in the first direction X, and this may be then reported to the user. On the contrary, when the first edge and the second edge of the virtual eighth test figure (TF8) go over the edges of two third organic patterns (OP3) that are separated with the first organic pattern (OP1) therebetween with reference to the fifth pixel figure (PF5) for the third pixel pattern (BP), it is confirmed that the deposition error is generated in the first direction X to the third organic patterns (OP3) that are separated in the second direction Y with reference to the third pixel pattern (BP) and are separated from each other in the first direction X, and this may be then reported to the user.

That is, the deposition errors of the third organic patterns (OP3) in the first direction X that are separated in the second direction Y with reference to the third pixel pattern (BP) and are separated from each other in the first direction X are checked by using the fifth pixel figure (PF5) and the eighth test figure (TF8).

The above-described checking whether the edge of the organic pattern 200 goes over the edge of the virtual test figure is performed by a controller including a terminal, and the checking of generation of the deposition error performed by the controller is displayed to the user through a display connected to the controller.

Accordingly, the method for testing an organic pattern according to the third exemplary embodiment photographs the test area (TA) including the pattern area (PA) and the non-pattern area (NPA) of the test substrate 100, a designated position, to acquire the test image (TI) that corresponds to the test area (TA), and the method checks whether the deposition errors are generated in the second direction Y of the first organic pattern (OP1), the second organic pattern (OP2), and the third organic pattern (OP3) by using the virtual first pixel figure (PF1), the second pixel figure (PF2), and the third pixel figure (PF3) displayed to the first pixel pattern (RP), the second pixel pattern (GP), and the third pixel pattern (BP) displayed in the pattern area (PA) of the test image (TI) and the virtual fourth test figure (TF4), the fifth test figure TF5, and the sixth test figure (TF6) displayed in the non-pattern area (NPA), thereby easily testing the organic pattern 200 deposited on the test substrate 100.

Further, the method for testing an organic pattern according to the third exemplary embodiment photographs the test area (TA) including the pattern area (PA) and the non-pattern area (NPA) of the test substrate 100, a designated position, to acquire the test image (TI) that corresponds to the test area (TA), and the method checks whether the deposition errors are generated in the first direction X of the first organic pattern (OP1) and the third organic pattern (OP3) by using the virtual fourth pixel figure (PF4) and the fifth pixel figure (PF5) displayed to the first pixel pattern (RP) and the third pixel pattern (BP) displayed in the pattern area (PA) of the test image (TI) and the virtual seventh test figure (TF7) and the eighth test figure (TF8) displayed in the non-pattern area (NPA), thereby easily testing the organic pattern 200 deposited on the test substrate 100.

That is, the method for testing an organic pattern for easily testing the deposition errors of the first organic pattern (OP1), the second organic pattern (OP2), and the third organic pattern (OP3) in the first direction X or the second direction Y for the first pixel pattern (RP), the second pixel pattern (GP), and the third pixel pattern (BP) formed on the single test substrate 100 rather than testing the deposition error on the single organic pattern 200 is provided.

This is information for changing process environments (e.g., a position of the substrate, a shape of the mask, a disposal of the mask, or a disposal of the deposition source) for forming one of the first organic pattern (OP1), the second organic pattern (OP2), and the third organic pattern (OP3) to which the deposition error is generated when the first organic pattern (OP1), the second organic pattern (OP2), and the third organic pattern (OP3) are respectively deposited on the substrate to be manufactured as the organic light emitting diode display, and it is provided to a manufacturer for manufacturing the organic light emitting diode display.

Particularly, the method for testing an organic pattern according to the third exemplary embodiment checks the deposition errors in the first direction X or the second direction Y of the first organic pattern (OP1), the second organic pattern (OP2), and the third organic pattern (OP3) corresponding to the first pixel pattern (RP), the second pixel pattern (GP), and the third pixel pattern (BP) to further precisely the deposition errors in the first direction X or the second direction Y of the first organic pattern (OP1), the second organic pattern (OP2), and the third organic pattern (OP3) and check distortion information of the mask or distortion information of the substrate formed by a fine metal mask (FMM). The information is provided to the manufacturer for manufacturing the organic light emitting diode display, and it functions as a factor for further precisely manufacturing the organic light emitting diode display on which the organic emission layer is deposited.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method for testing an organic pattern, comprising:
   forming an organic pattern on a test substrate through a mask;
   acquiring a test image by photographing a predetermined test area of the test substrate; and
   checking whether the edge of the organic pattern displayed to the test image overlaps an edge of a virtual test figure,
   wherein the test substrate includes a pattern area in which a first pixel pattern, a second pixel pattern, and a third pixel pattern neighbor each other, and a non-pattern area neighboring the pattern area, and the acquiring of the test image is performed by photographing the predetermined test area including the pattern area and the non-pattern area, and
   wherein the forming of an organic pattern on a test substrate through a mask includes;
   forming a plurality of first organic patterns for covering the first pixel pattern of the pattern area and a first section of the non-pattern area on the test substrate through a first mask;
   forming a plurality of second organic patterns for covering the second pixel pattern of the pattern area and a second section of the non-pattern area on the test substrate through a second mask; and
   forming a plurality of third organic patterns for covering the third pixel pattern of the pattern area and a third section of the non-pattern area on the test substrate through a third mask.

2. The method of claim 1, wherein
   the checking of whether an edge of the organic pattern displayed to the test image goes over an edge of a virtual test figure includes:
   checking whether an edge of the plurality of first organic patterns goes over an edge of a virtual first test figure displayed to the first section of the non-pattern area;
   checking whether an edge of the plurality of second organic patterns goes over an edge of a virtual second test figure displayed to the second section of the non-pattern area; and
   checking whether an edge of the plurality of third organic patterns goes over an edge of a virtual third test figure displayed to the third section of the non-pattern area.

3. The method of claim 2, wherein
   depths of the first test figure, the second test figure, and the third test figure in a first direction correspond to depths of the first pixel pattern, the second pixel pattern, and the third pixel pattern in the first direction.

4. The method of claim 3, wherein
   the first test figure is separated from the first pixel pattern with the plurality of second organic patterns therebetween,
   the second test figure is separated from the second pixel pattern with the plurality of first organic patterns therebetween, and
   the third test figure is separated from the third pixel pattern with the plurality of second organic patterns therebetween.

5. The method of claim 4, wherein
   the first test figure. the second test figure, and the third test figure respectively have a figure shape of a different size.

6. The method of claim 3, wherein
   the first test figure is provided between the neighboring first pixel patterns,
   the second test figure is provided between the neighboring second pixel patterns, and
   the third test figure is provided between the neighboring third pixel patterns.

7. The method of claim 6, wherein
   the first test figure, the second test figure, and the third test figure respectively have a figure shape of a same size.

8. The method of claim 1, wherein
   the plurality of second organic patterns are extended in a first direction and are separated from each other in a second direction crossing, the first direction, the plurality of first organic patterns are separated from the plurality of third organic patterns M the second direction with the plurality of second organic patterns therebetween, and the plurality of third organic patterns neighbor the plurality of first organic patterns in the first direction, and the checking of whether an edge of the organic pattern displayed to the test image goes over an edge of a virtual test figure includes:
checking whether each edge of the first pixel pattern is provided inside two virtual first pixel figures disposed in the second direction, and checking whether a first edge and a second edge of a virtual fourth test figure having a center area separated from the two virtual first pixel figures of the first pixel pattern in the first direction and extended in the second direction go over an edge of the plurality of second organic patterns covering, the second pixel pattern and an edge of the plurality of second organic patterns covering the second section;
checking whether each edge of the second pixel pattern is provided inside two virtual second pixel figures disposed in the second direction, and checking whether a first edge and a second edge of a virtual fifth test figure having a center area separated from the two virtual second pixel figures of the second pixel pattern in the first direction and extended in the second direction go over an edge of the plurality of third organic patterns covering the third pixel pattern and an edge of the plurality of first organic patterns covering the first section; and
checking whether each edge of the third pixel pattern is provided inside two virtual third pixel figures disposed in the second direction, and checking whether a first edge and a second edge of a virtual sixth test figure having a center area separated from the two virtual third pixel figures in the first direction and extended in the second direction go over an edge of the plurality of second organic patterns covering, the second pixel pattern and an edge of the plurality of second organic patterns covering the second section.

9. The method of claim 8, wherein
the plurality of first organic patterns are separated from each other in the first direction with the plurality of third organic patterns therebetween, and
the checking of whether an edge of the organic pattern displayed to the test image goes over an edge of a virtual test figure further includes:
checking whether each edge of the first pixel pattern is provided inside two virtual fourth pixel figures disposed in the first direction, and checking whether a first edge and a second edge of a virtual seventh test figure having a center area separated from the two virtual fourth pixel figures in the second direction and extended in the first direction go over edges of the two first organic patterns that are separated with the plurality of third organic patterns therebetween; and
checking whether each edge of the third pixel pattern is provided inside two virtual fifth pixel figures disposed in the first direction, and checking whether a first edge and a second edge of a virtual eighth test figure having a center area separated from the two virtual fifth pixel figures in the second direction and extended in the first direction go over edges of the two third organic patterns separated with the plurality of first organic patterns therebetween.

10. A method for testing an organic pattern, comprising:
forming a plurality of organic patterns on a test substrate through a mask
acquiring a test image by photographing a predetermined test area of the test substrate, said test image having a rectangular shape with four edges;
checking whether any of the four edges of an organic pattern of the plurality of organic patterns displayed to the test image goes over an edge of a virtual test figure; and
rejecting the organic pattern when any of the four edges of any of the plurality of organic patterns displayed to the test image goes over an edge of a corresponding virtual test figure,
wherein the test substrate includes a pattern area in which a first pixel pattern, a second pixel pattern, and a third pixel pattern neighbor each other, and a non-pattern area neighboring the pattern area, and the acquiring of a test image is performed by photographing the test area including the pattern area and the non-pattern area, and
wherein the forming of a plurality of organic patterns on a test substrate through a mask includes:
forming a plurality of first organic patterns for covering the first pixel pattern of the the pattern area and a first section of the non-pattern area on the test substrate through a first mask;
forming a plurality of second organic patterns for covering the second pixel pattern of the pattern area and a second section of the non-pattern area on the test substrate through a second mask; and
forming a plurality of third organic patterns for covering, the third pixel pattern of the pattern area and a third section of the non-pattern area on the test substrate through a third mask.

11. The method of claim 10, wherein
the checking of whether an edge of any one of the plurality of organic patterns displayed to the test image goes over an edge of a virtual test figure includes:
checking whether an edge of the plurality of first organic patterns goes over an edge of a virtual first test figure displayed to the first section of the non-pattern area;
checking whether an edge of the plurality of second organic patterns goes over an edge of a virtual second test figure displayed to the second section of the non-pattern area; and
checking whether an edge of the plurality of third organic patterns goes over an edge of a virtual third test figure displayed to the third section of the non-pattern area.

12. The method of claim 11, wherein
depths of the first test figure, the second test figure, and the third test figure in a first direction correspond to depths of the first pixel pattern, the second pixel pattern, and the third pixel pattern in the first direction.

13. The method of claim 12, wherein
the first test figure is separated from the first pixel pattern with the plurality of second organic patterns therebetween,
the second test figure is separated from the second pixel pattern with the plurality of first organic patterns therebetween, and
the third test figure is separated from the third pixel pattern with the plurality of second organic patterns therebetween.

14. The method of claim 13, wherein
the first test figure, the second test figure, and the third test figure respectively have a figure shape of a different size.

15. The method of claim 12, wherein
the first test figure is provided between the neighboring first pixel patterns,
the second test figure is provided between the neighboring second pixel patterns, and
the third test figure is provided between the neighboring third pixel patterns.

16. The method of claim 15, wherein the first test figure, the second test figure, and the third test figure respectively have a figure shape of a same size.

* * * * *